(12) United States Patent
Miller, III

(10) Patent No.: US 12,048,465 B2
(45) Date of Patent: Jul. 30, 2024

(54) STERNAL CLOSURE DEVICE WITH DUAL LOCKING MECHANISM

(71) Applicant: MAVREK Medical, LLC, Tulsa, OK (US)

(72) Inventor: Archibald S. Miller, III, Tulsa, OK (US)

(73) Assignee: Mavrek Medical, LLC, Tulsa, OK (US)

( * ) Notice: Subject to any disclaimer, the term of this patent is extended or adjusted under 35 U.S.C. 154(b) by 328 days.

(21) Appl. No.: 17/421,209

(22) PCT Filed: Jan. 9, 2020

(86) PCT No.: PCT/US2020/012978
§ 371 (c)(1),
(2) Date: Jul. 7, 2021

(87) PCT Pub. No.: WO2020/146669
PCT Pub. Date: Jul. 16, 2020

(65) Prior Publication Data
US 2022/0117638 A1    Apr. 21, 2022

Related U.S. Application Data

(60) Provisional application No. 62/790,409, filed on Jan. 9, 2019.

(51) Int. Cl.
*A61B 17/80* (2006.01)
*A61B 17/82* (2006.01)
*A61B 17/00* (2006.01)

(52) U.S. Cl.
CPC ...... *A61B 17/8009* (2013.01); *A61B 17/8076* (2013.01); *A61B 17/823* (2013.01); *A61B 2017/00407* (2013.01)

(58) Field of Classification Search
CPC ............ A61B 17/8009; A61B 17/8023; A61B 17/8076; A61B 17/823
See application file for complete search history.

(56) References Cited

U.S. PATENT DOCUMENTS

| 268,632 A | 12/1882 | Danforth |
| 380,093 A | 3/1888 | Cruice et al. |

(Continued)

FOREIGN PATENT DOCUMENTS

| CN | 103211632 A | 7/2013 |
| CN | 104107084 A | 10/2014 |
| CN | 106108995 A | 11/2016 |

OTHER PUBLICATIONS

European Search Report and Opinion for PCT/US2020/012978 dated Sep. 14, 2022.

(Continued)

*Primary Examiner* — Larry E Waggle, Jr.
(74) *Attorney, Agent, or Firm* — Crowe & Dunlevy, P.C.

(57) ABSTRACT

A sternal closure device includes an insertion member, a receiver member and a joint locking mechanism. The joint locking mechanism includes a dual pawl assembly and a dual ratchet assembly. The dual pawl assembly includes a pair of pawl arms that include heads with outward facing teeth. The dual ratchet assembly includes a pair of ratchet arms with inward facing teeth that are configured for an intermeshed engagement with the teeth on the corresponding pawl arms. Alignment tabs on the ratchet arms are captured within guide channels on the receiver member. The configuration and number of the teeth contribute to the strength of the device. The locking mechanism contributes to efficiency, speed, and strength of the closure.

10 Claims, 9 Drawing Sheets

(56) References Cited

U.S. PATENT DOCUMENTS

| | | | |
|---|---|---|---|
| 3,385,299 A | 5/1968 | Le | |
| 3,971,384 A | 7/1976 | Hasson | |
| 4,201,215 A | 5/1980 | Crossett et al. | |
| 5,061,007 A | 10/1991 | Simpson | |
| 5,092,889 A | 3/1992 | Campbell | |
| 5,584,835 A | 12/1996 | Greenfield | |
| 5,941,881 A | 8/1999 | Barnes | |
| 5,964,763 A | 10/1999 | Incavo et al. | |
| 6,007,538 A | 12/1999 | Levin | |
| 6,051,007 A | 4/2000 | Hogendijk et al. | |
| 6,217,580 B1 | 4/2001 | Levin | |
| 6,540,769 B1 | 4/2003 | Miller | |
| 6,712,821 B2 | 3/2004 | Gabbay | |
| 6,872,210 B2 | 3/2005 | Hearn | |
| 6,969,398 B2 * | 11/2005 | Stevens | A61B 17/8009 606/217 |
| 7,033,377 B2 | 4/2006 | Miller | |
| 7,749,256 B2 * | 7/2010 | Farris | A61B 17/7059 606/282 |
| 7,803,176 B2 | 9/2010 | Teague et al. | |
| 8,172,887 B2 | 5/2012 | Gabele | |
| 2002/0038147 A1 | 3/2002 | Miller | |
| 2002/0143336 A1 | 10/2002 | Hearn | |
| 2002/0188296 A1 | 12/2002 | Michelson | |
| 2003/0083694 A1 | 5/2003 | Miller | |
| 2005/0267475 A1 | 12/2005 | Miller | |
| 2005/0277939 A1 | 12/2005 | Miller | |
| 2006/0167458 A1 | 7/2006 | Gabele | |
| 2006/0195101 A1 | 8/2006 | Stevens | |
| 2006/0235398 A1 | 10/2006 | Farris et al. | |
| 2009/0118774 A1 | 5/2009 | Miller | |
| 2009/0118775 A1 | 5/2009 | Burke | |
| 2009/0138054 A1 | 5/2009 | Teague et al. | |
| 2009/0248091 A1 | 10/2009 | Teague et al. | |
| 2010/0145386 A1 * | 6/2010 | Greenhalgh | A61B 17/8863 606/279 |
| 2011/0034958 A1 | 2/2011 | Anderson et al. | |
| 2011/0054547 A1 | 3/2011 | Anderson | |
| 2011/0313474 A1 | 12/2011 | Gabele | |
| 2012/0245644 A1 | 9/2012 | Teague et al. | |

OTHER PUBLICATIONS

ISA/US; Search Report and Written Opinion for PCT/US19/12978; dated Mar. 24, 2020.

* cited by examiner

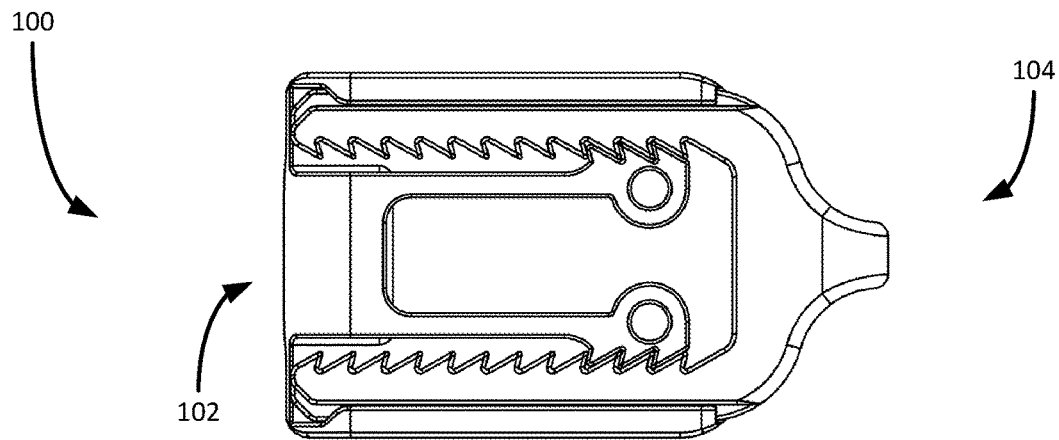
FIG. 14A
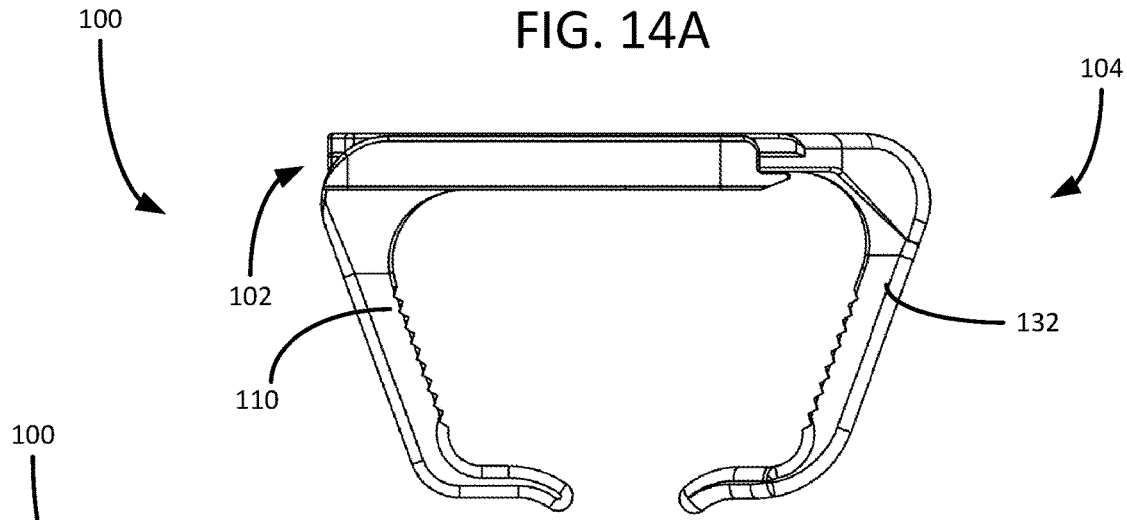
FIG. 14B
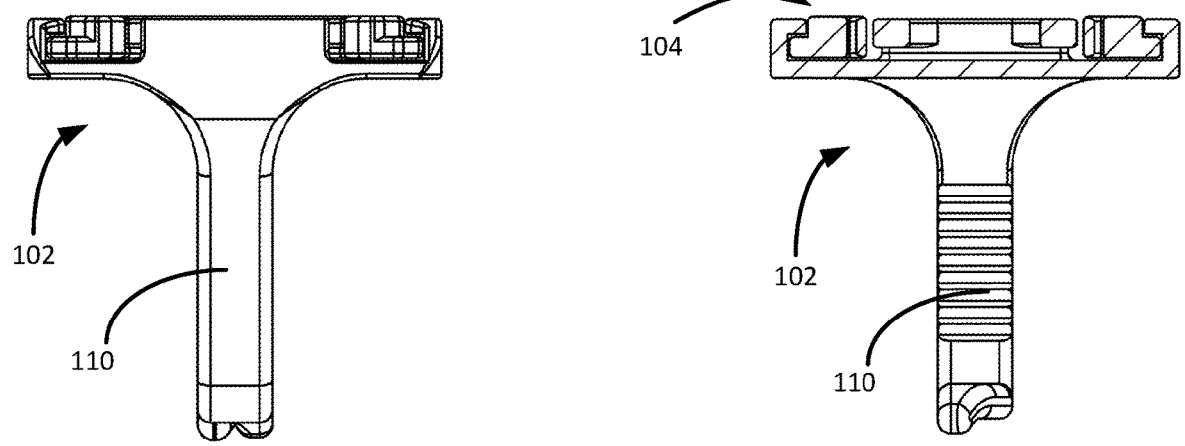
FIG. 14C
FIG. 14D

STERNAL CLOSURE DEVICE WITH DUAL LOCKING MECHANISM

RELATED APPLICATIONS

This application claims the benefit of U.S. Provisional Patent Application Ser. No. 62/790,409 entitled "Sternal Closure Device with Dual Locking Mechanism" filed Jan. 9, 2019, the disclosure of which is herein incorporated by reference.

FIELD OF INVENTION

The present invention relates generally to surgical positioning devices and more particularly to a surgical device for capturing, positioning, aligning, and stabilizing portions of a severed human sternum.

BACKGROUND OF INVENTION

Wire closures are widely represented in the contemporary art as a recognized means for closing the sternum following a mid-line sternotomy. Wire-based closure devices nonetheless suffer from several deficiencies. First, the average implementation/deployment time is 15-20 minutes per wire closure. Such an excessive time requirement translates into increased operating room costs, increased doctor, staff and insurance costs, and increased doctor fatigue. Second, a variety of disruptive forces frustrate the very intention of wire-based systems. Third, the current plating systems fail to provide three-dimensional stabilization of the fractured sternal segments thereby allowing displacement of the segments. Anatomic forces associated with sternotomies include the rectus abdominus muscles exerting an uneven and shearing displacement pull, a lateral and diagonal pull by pectoralis muscles, forces generated by Valsalva action and anterior/posterior displacement by intervertebral muscles of the hemi-sternum via respiratory muscle action.

In view of the deficiencies of wire-based clamping and plating surgical devices, and further in view of the life threatening conditions associated with failure of such devices, newer clamp closure technology has been recognized as superior to the traditional wire closure systems. These devices recognize the three dimensional forces at work in an anatomically moving system and stabilize in a superior fashion. Circumferential clamp closures typically include two primary elements that can be removably associated with one another. As in U.S. Pat. No. 6,051,007 issued Apr. 18, 2000 to Hogendijk et al., ("Hogendijk '007"), several prior art clamp closures include two clamp elements that each include a "leg" portion configured to grasp an opposing side of a vertically severed sternum. When approximated, the two clamp elements draw the severed sternum into a closed position, and stabilize the sternum in a three dimensional fashion. A locking feature is used to hold the clamp closures in the approximated position.

Although generally effective, prior art clamp closures suffer several deficiencies. For example, many locking mechanisms used in prior art closures fail under increased stress loads. Other locking mechanisms are difficult to manipulate or impossible to quickly remove under emergency conditions. Other devices possess multiple parts or segments which must be articulated, and spot welded, thus increasing chances of device failure. It is to these and other deficiencies in the prior art that the present invention is directed.

SUMMARY OF THE INVENTION

A sternal closure device includes an insertion member, a receiver member and a joint locking mechanism. The joint locking mechanism includes a dual pawl assembly and a dual ratchet assembly. The dual pawl assembly includes a pair of pawl arms that include heads with outward facing teeth. The dual ratchet assembly includes a pair of ratchet arms with inward facing teeth that are configured for an intermeshed engagement with the teeth on the corresponding pawl arms. Alignment tabs on the ratchet arms are captured within guide channels on the receiver member.

BRIEF DESCRIPTION OF DRAWINGS

FIG. 14A is a top view of a single-leg embodiment of the sternal closure device.

FIG. 14B is a side view of the single leg embodiment of FIG. 14A.

FIG. 14C is an end view of the single leg embodiment of FIG. 14A.

FIG. 14D is a cross-sectional view of the single leg embodiment of FIG. 14A.

WRITTEN DESCRIPTION

Figure 1:
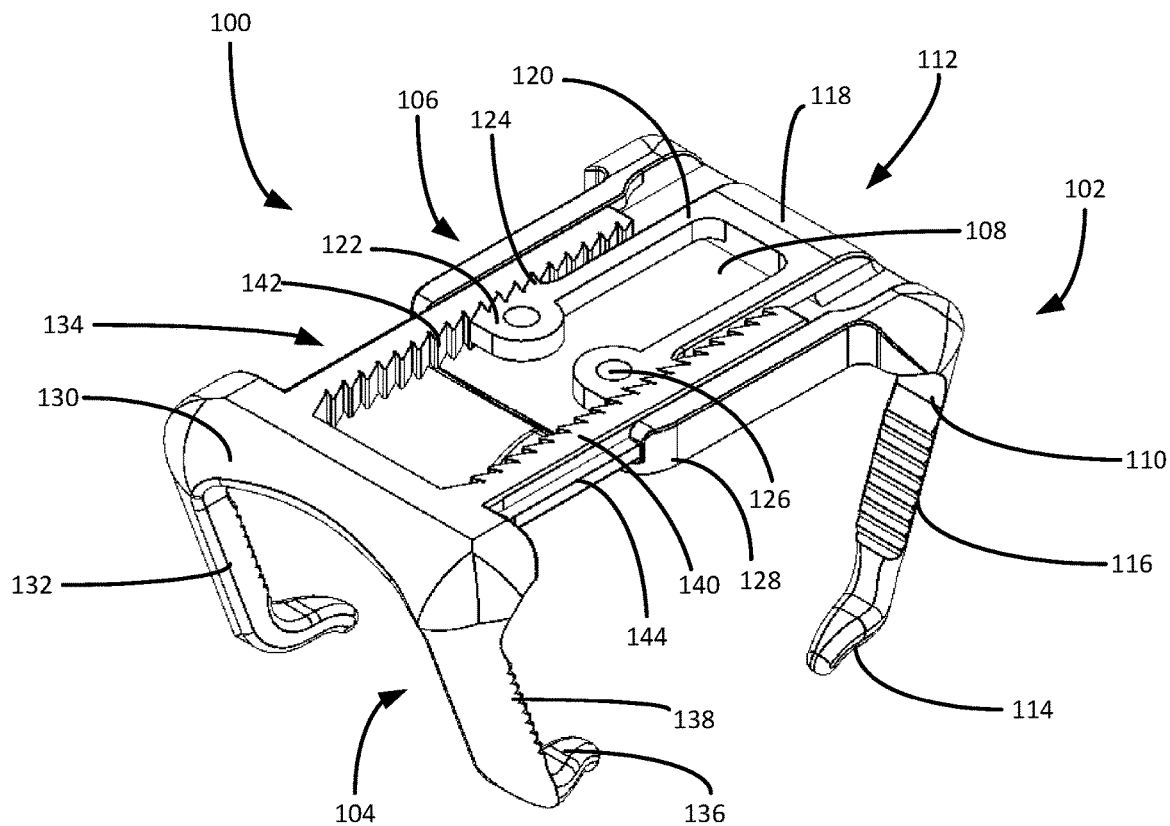
FIG. 1 is a front perspective view of a sternal closure device constructed in accordance with an embodiment of the present invention.

FIGS. 1-4 and FIGS. 14A-14D provide various views of a sternal closure device 100 constructed in accordance with an exemplary embodiment. The sternal closure device 100 can be generally characterized as a two-piece articulating clamp in which a receiver member 102 engages with an insertion member 104. The receiver member 102 and insertion member 104 are presented as distinct, separable components. When joined together, the insertion member 104 is retained within the receiver member 102 in a locking relationship as the insertion member 104 is advanced within the receiver member 102. The receiver and insertion members 102, 104 are secured together by a joint locking mechanism 106 that prevents the insertion member 104 from being withdrawn from the receiver member 102 except when the joint locking mechanism 106 is intentionally released by an operator. The receiver member 102, which may be characterized as a "female" clamp portion, is illustrated in isolation in FIGS. 5-8 and FIGS. 16A-16B. The insertion member 104, which may be characterized as a "male" clamp portion, is illustrated in isolation in FIGS. 9-13 and FIGS. 15A-15B.

As disclosed below, the sternal closure device 100 includes a number of components that cooperatively perform the intended function of positioning, aligning and securing a severed sternum. It will be understood that although the present disclosure explicitly covers various embodiments, there are additional embodiments that are also encompassed within the scope of the present invention. It will be further understood that the sternal closure device 100 can be sized and configured for use on patients across a wide range of sizes and variations in anatomies. Unless otherwise noted, each component of the sternal closure device 100 is constructed from a suitable surgical-grade metal alloy, ceramic or hardened plastic.

The receiver member 102 includes a receiver member base 108, one or more receiver member legs 110 and a dual pawl assembly 112. The receiver member legs 110 extend downward and forward from the back of the receiver member base 108. In the embodiments depicted in FIGS. 1-12, the receiver member legs 110 are spaced apart by a distance (d1) that can be sized and configured to capture a rib. In the embodiments depicted in FIGS. 16A-16B, the receiver member 102 includes a single receiver member leg 110 that is sized and configured to fit between a pair of ribs attached to the severed sternum.

Figure 3:
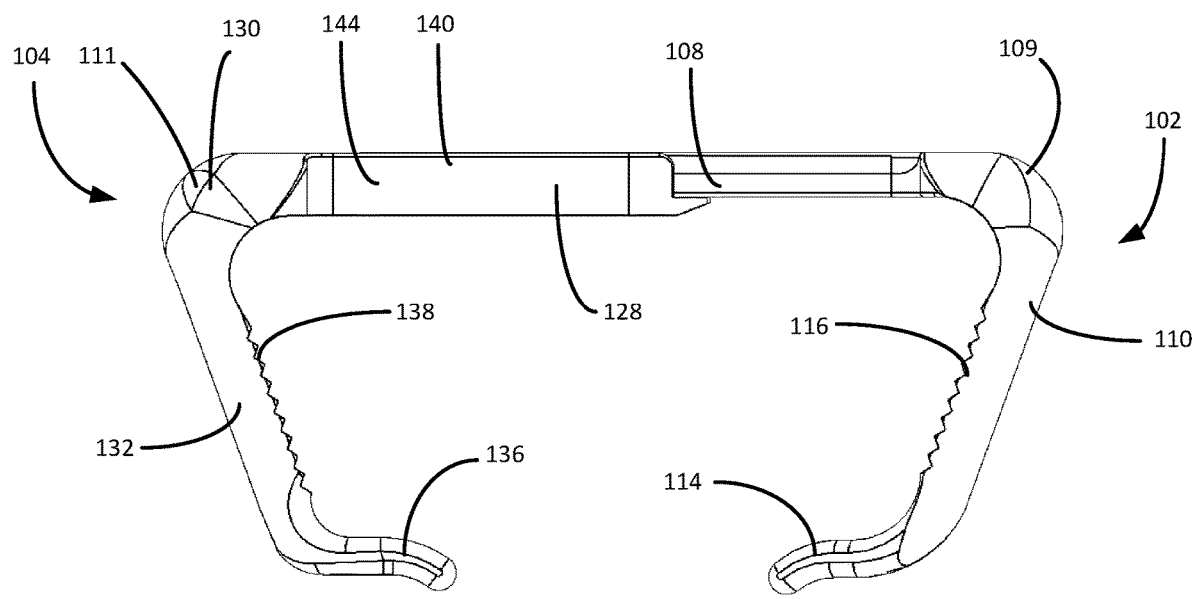
FIG. 3 is a side view of the sternal closure device of FIG. 3.
Figure 4:
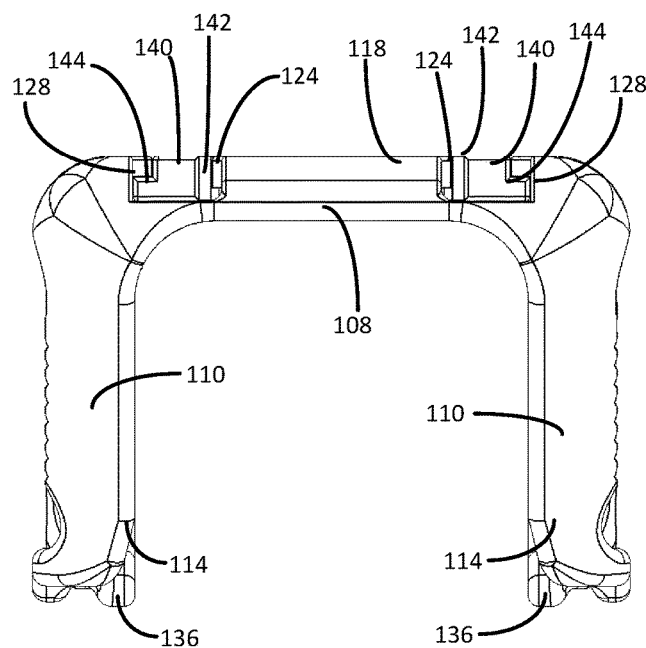
FIG. 4 is an end view of the sternal closure device of FIG. 1.
Figure 6:
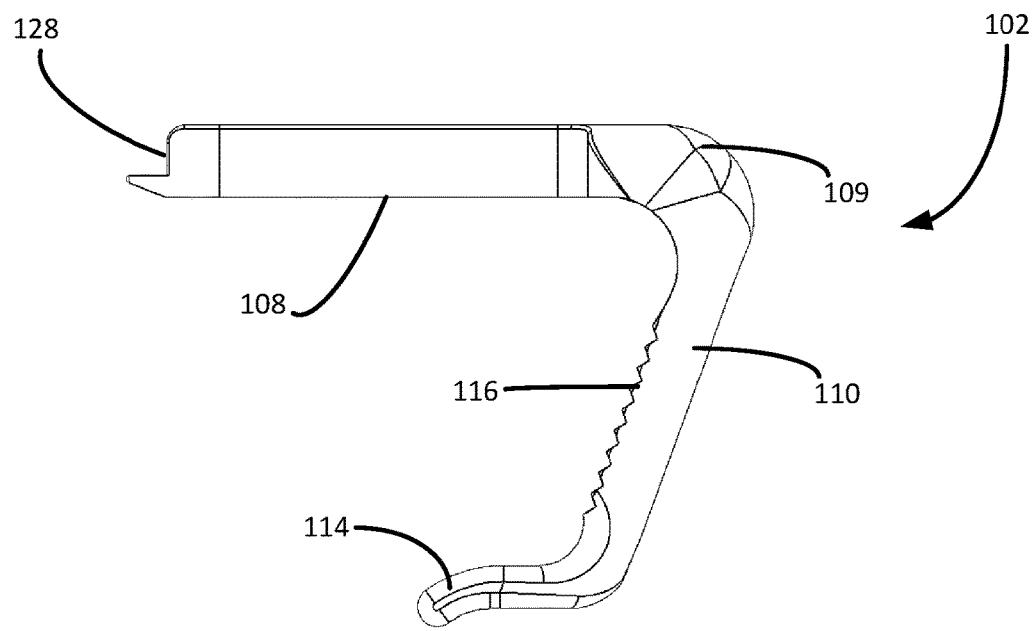
FIG. 6 is a side view of the receiver member of FIG. 5.

The receiver member base 108 includes rounded shoulders 109 above the receiver member legs 110. The rounded shoulders 109 improve comfort and reduce the risk of wound dehiscence. The receiver member legs 110 may each include feet 114 that are configured to contact a posterior side of the sternum. The receiver member legs 110 may also include a textured surface 116 that is configured to increase frictional contact with a lateral portion of the sternum. Thus, as best seen in FIGS. 3, 6 and 14B, the receiver member base 108 and receiver member legs 110 cooperate to form a crescent or "C-shape" that is sized and configured to capture and partially surround approximately one half of the severed sternum.

Figure 5:
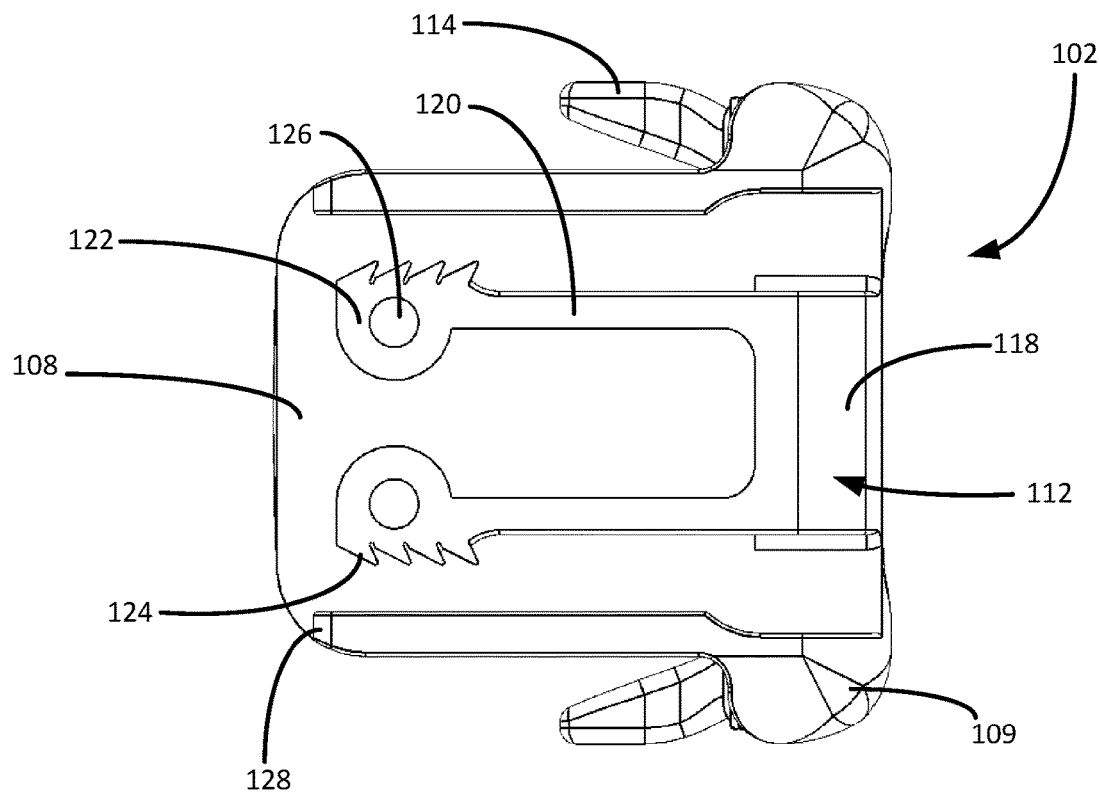
FIG. 5 is a top view of the receiver member of the sternal closure device of FIG. 1.
Figure 7:
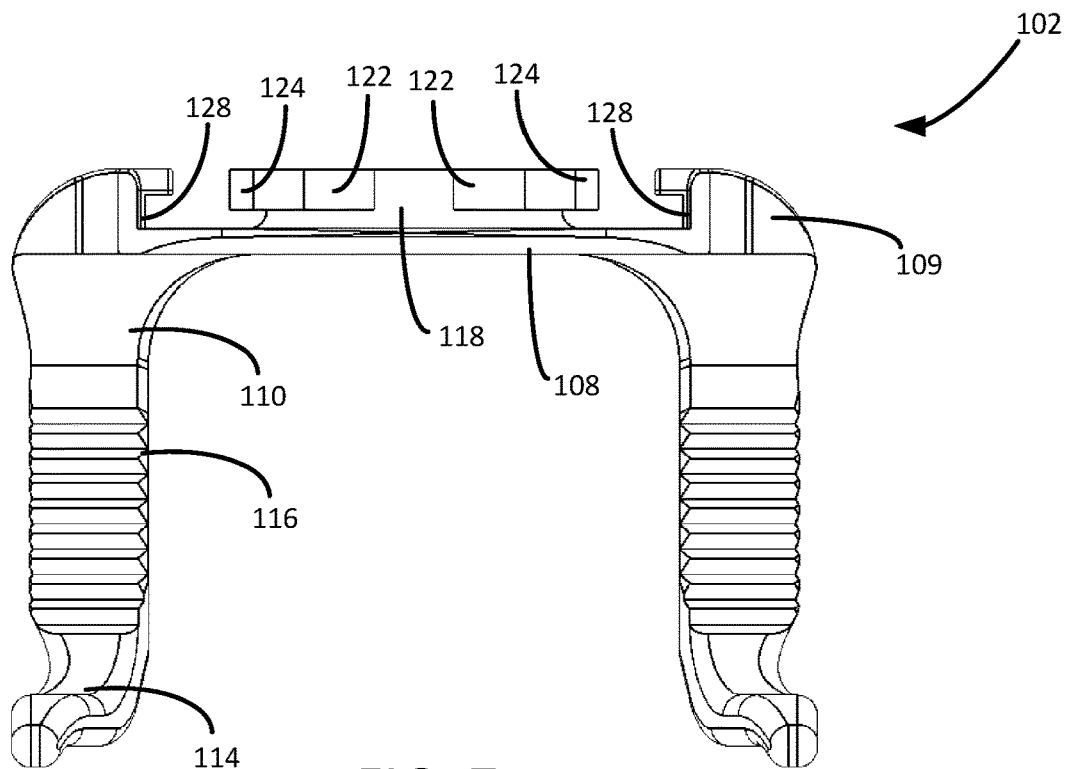
FIG. 7 is an end view of the receiver member of FIG. 5.

The dual pawl assembly 112 includes a pawl block 118 that extends upward from the top surface of the receiver member base 108. Pawl arms 120 extend forward from the top of the pawl block 118. As illustrated in FIG. 7, the pawl block 118 raises the pawl arms 120 above the top surface of the receiver member base 108. Each pawl arm 120 includes a head 122 located on the distal end of the pawl arm 120. The head 122 includes a series of outward facing pawl teeth 124 and a tool aperture 126. As illustrated in FIG. 5, the pawl arms 120 and heads 122 are laterally spaced apart.

In exemplary embodiments, each component of the dual pawl assembly 112 is constructed from a metal or metal alloy that permits the pawl arms 120 to slightly deflect inward when a sufficient lateral force is applied to the outside of the pawl arms 120, or when a sufficient compressive force is applied to the pawl arms 120 through the tool apertures 126 in the pawl heads 122. The lateral force can be applied by the insertion member 104 when the insertion member 104 is engaged within the receiver member 102. The lateral compressive force can also be applied to the pawl arms 120 by engaging release pliers (not shown) in the tool apertures 126.

In exemplary embodiments, the dual pawl assembly 112 is manufactured as unitary, integral component together with the balance of the receiver member 102. In these embodiments, the dual pawl assembly 112 is permanently fixed to, or made as part of, the receiver member base 108. In other embodiments, the pawl block 118 can be configured for attachment to the receiver member base 108 by removable fasteners, such as a stud and lock-nut mechanism.

Figure 8:
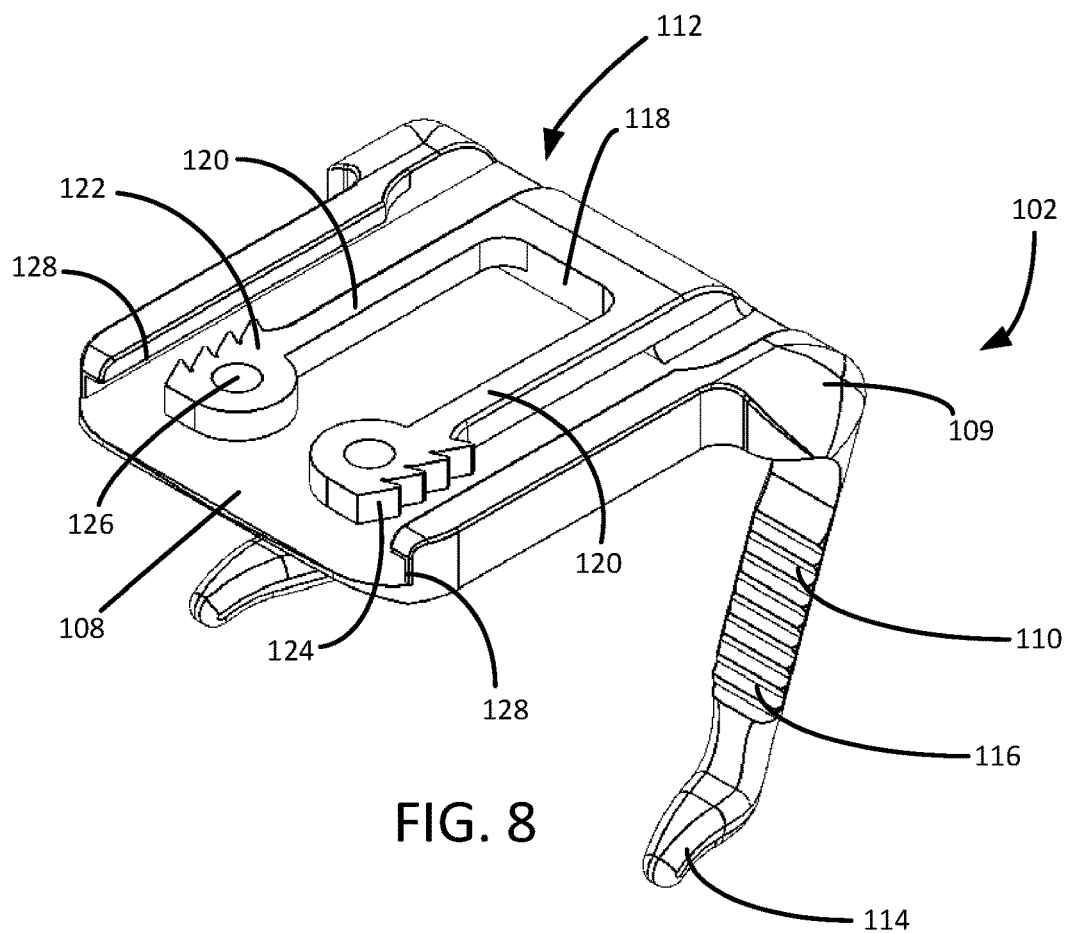
FIG. 8 is a top perspective view of the receiver member of FIG. 5.
Figure 9:
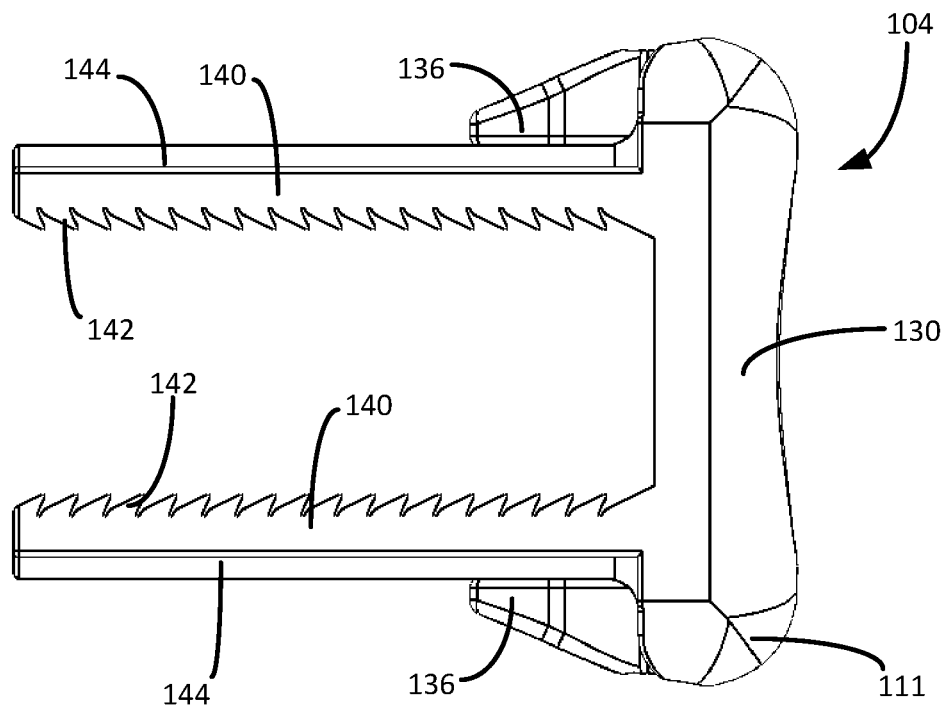
FIG. 9 is a top view of the insertion member of the sternal closure device of FIG. 1.

The receiver member 102 further includes channels 128 that extend along the top of the receiver member base 108. The channels 128 extend substantially parallel to the pawl arms 120. The channels 128 can be manufactured as part of a unitary component of the receiver member base 108. In this way, the entire receiver member 102 can be manufactured as unitary piece through milling, casting, forging or additive manufacturing processes. As best indicated in FIGS. 7-8, the channels 128 include an upper overhang that cooperates with the receiver member base 108 to form a boxed receiver that has lower, side and upper walls that are configured to receive and capture the insertion member 104.

Turning to FIGS. 9-13 and FIGS. 15A-15B, shown therein are isolated views of the insertion member 104. The insertion member 104 includes an insertion member base 130, one or more insertion member legs 132 and a dual ratchet assembly 134. The insertion member 104 includes rounded shoulders 111 above the insertion member legs 132. The rounded shoulders 111 improve comfort and reduce the risk of wound dehiscence. The one or more insertion member legs 132 extend downward and forward from the back of the insertion member base 130. In the embodiment depicted in FIGS. 9-13, the insertion member 104 includes a pair of insertion member legs 132 that are spaced apart by a distance (d2). In some embodiments, the distance (d2) between the insertion member legs 132 is sized to surround a rib attached to the severed sternum. The distance (d2) between the insertion member legs 132 can be larger, smaller or the same size as the distance (d1) between the receiver member legs 110. In the single-leg embodiment depicted in FIGS. 15A-15B, the insertion member 104 includes a single insertion member leg 132 that can be sized and configured to fit between a pair of ribs attached to the severed sternum.

Figure 10:
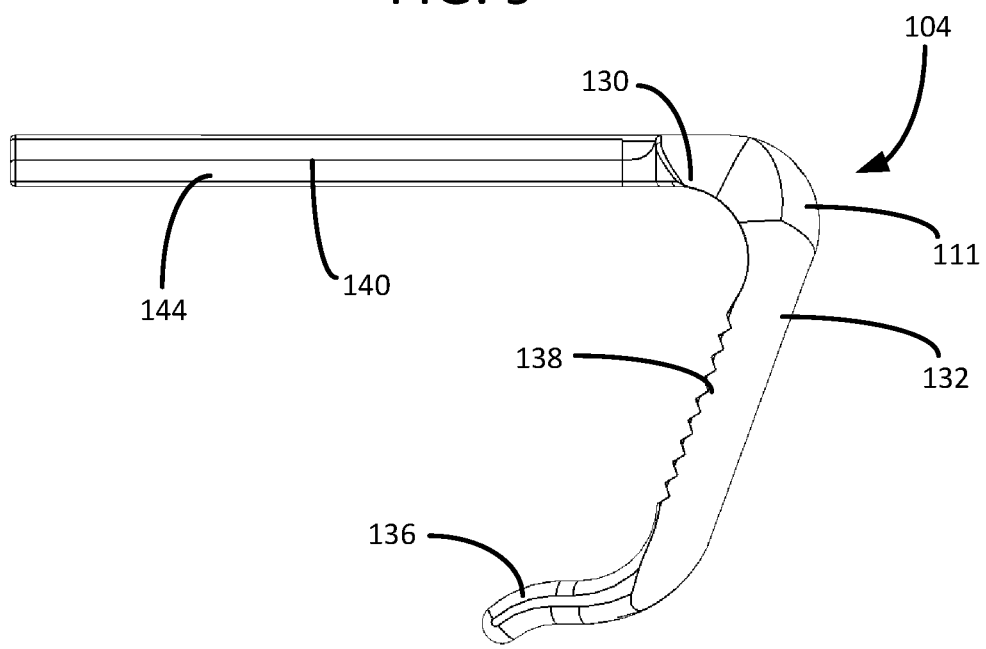
FIG. 10 is a side view of the insertion member of FIG. 5.
Figure 11:
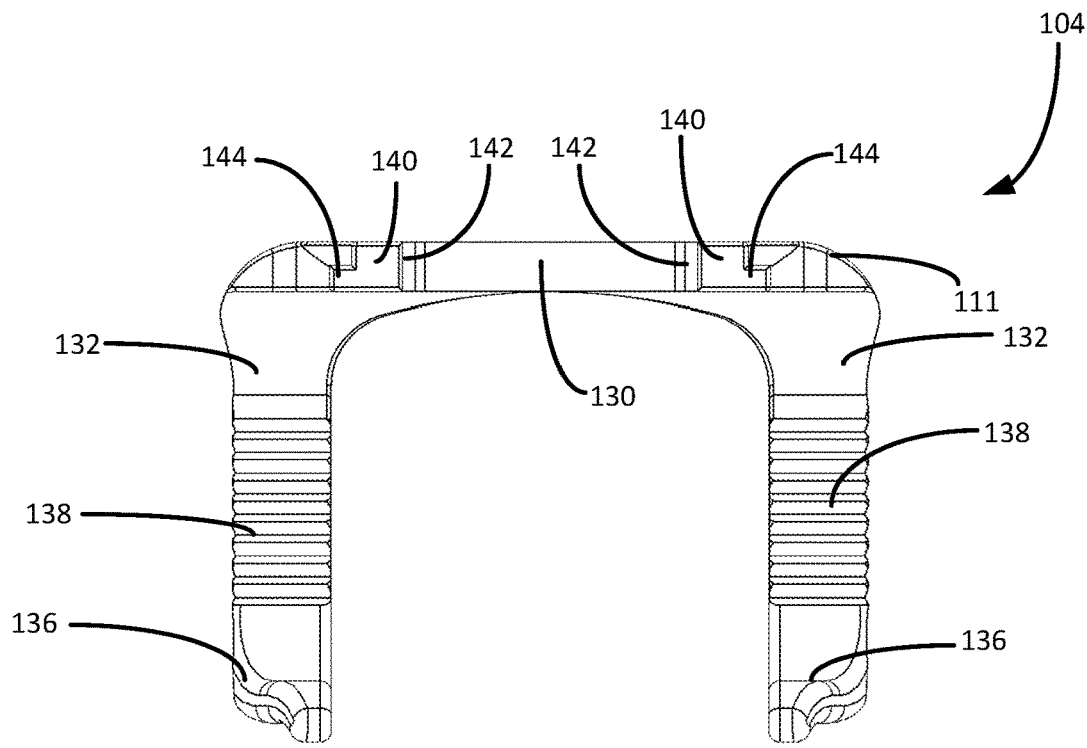
FIG. 11 is an end view of the insertion member of FIG. 5.
Figure 12:
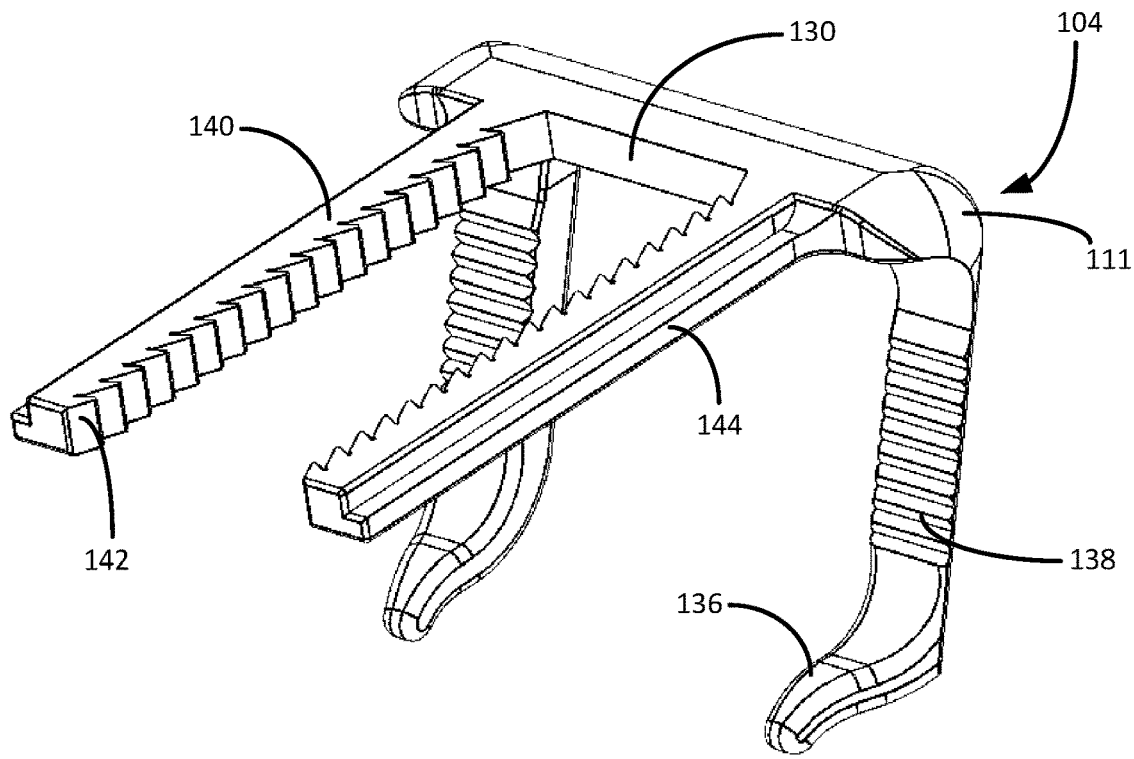
FIG. 12 is a top perspective view of the insertion member of FIG. 5.

The insertion member legs 132 may each include feet 136 that are configured to contact a posterior side of the sternum. The insertion member legs 132 may also include a textured surface 138 that is configured to increase frictional contact with a lateral portion of the sternum. Thus, as best seen in FIGS. 3, 10 and 14B, the insertion member base 130 and insertion member legs 132 cooperate to form a crescent or "C-shape" that is sized and configured to capture and partially surround approximately one half of the severed sternum.

Figure 13A:
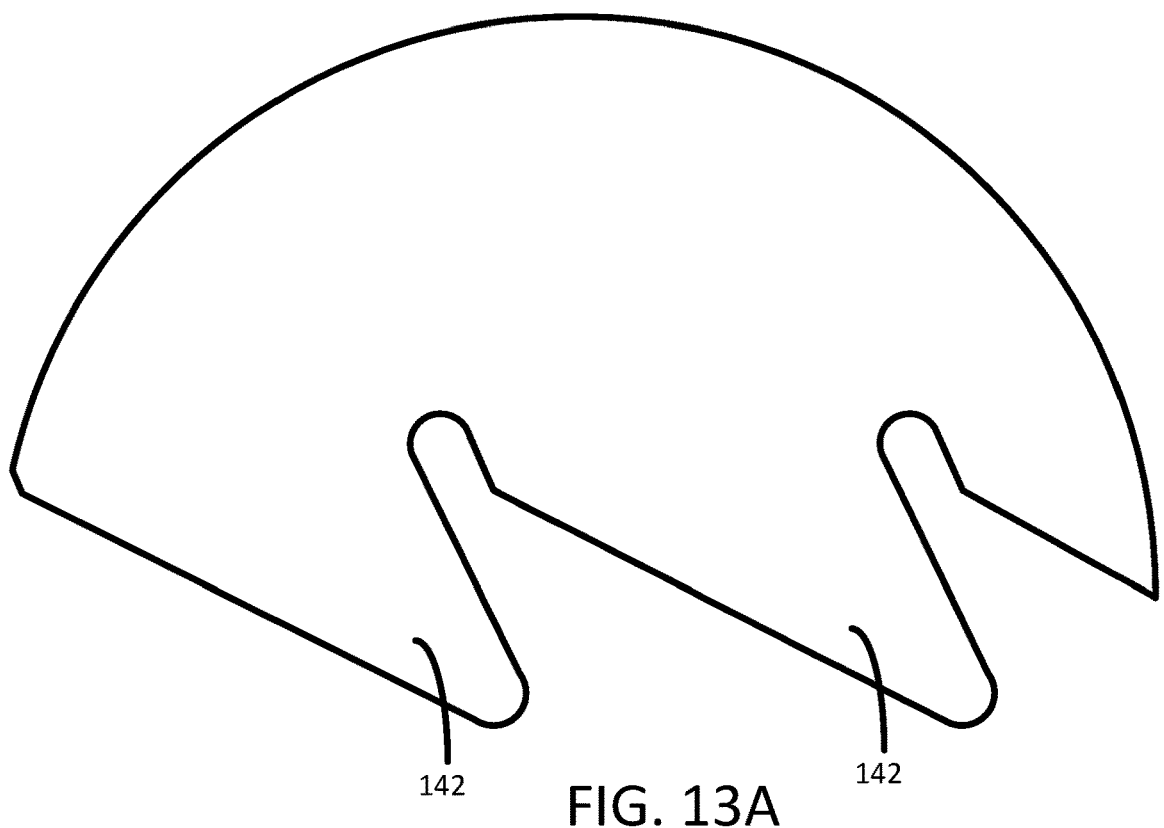
FIG. 13A is a close-up view of a portion of the teeth on a first embodiment of the insertion member of FIG. 5.
Figure 13B:
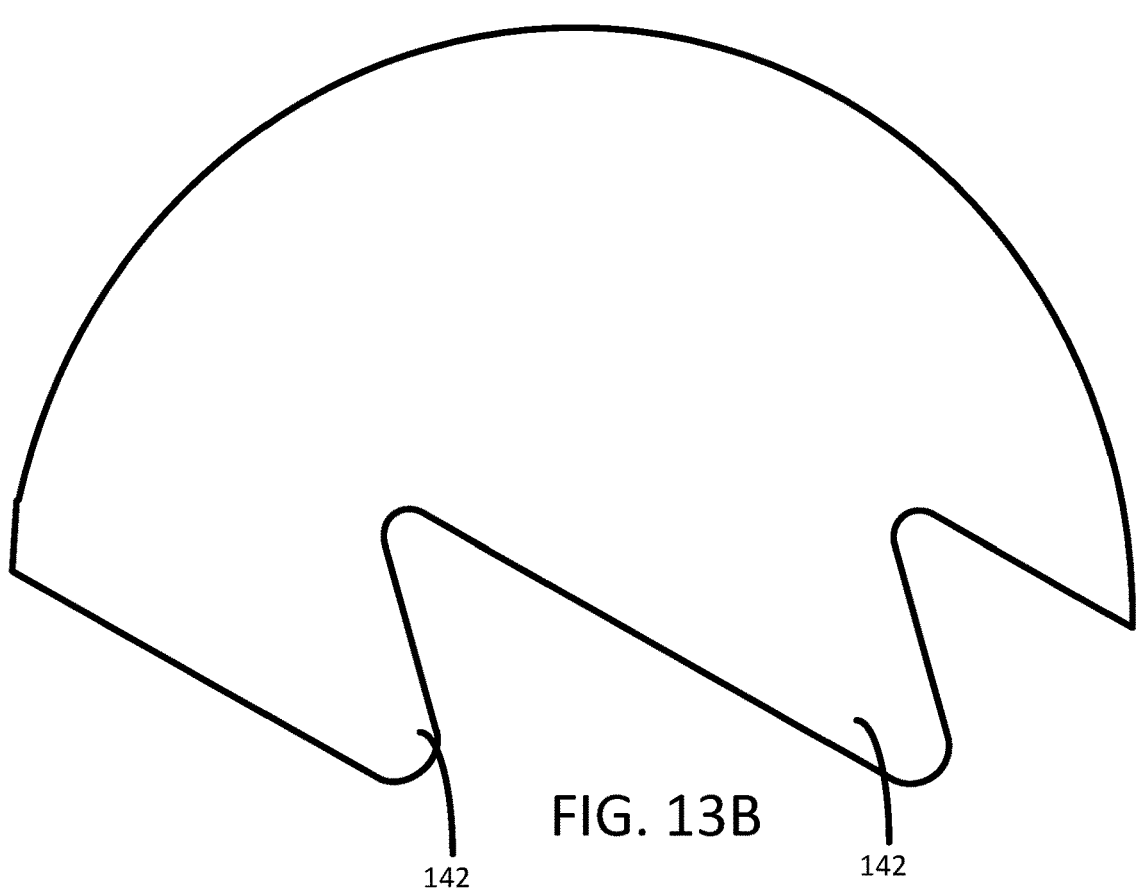
FIG. 13B is a close-up view of a portion of the teeth on a second embodiment of the insertion member of FIG. 5.
Figure 15A:
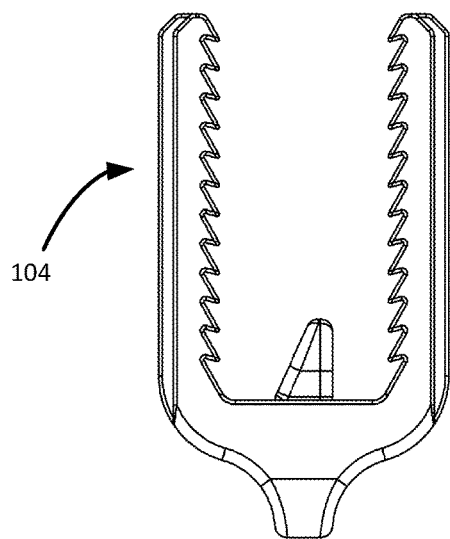
FIG. 15A and FIG. 15B are top and top perspective views, respectively, of the insertion member of the single leg embodiment of FIG. 14A.
Figure 15B:
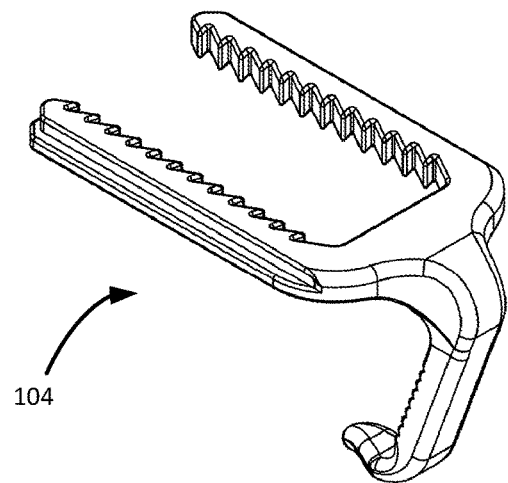
Figure 16A:
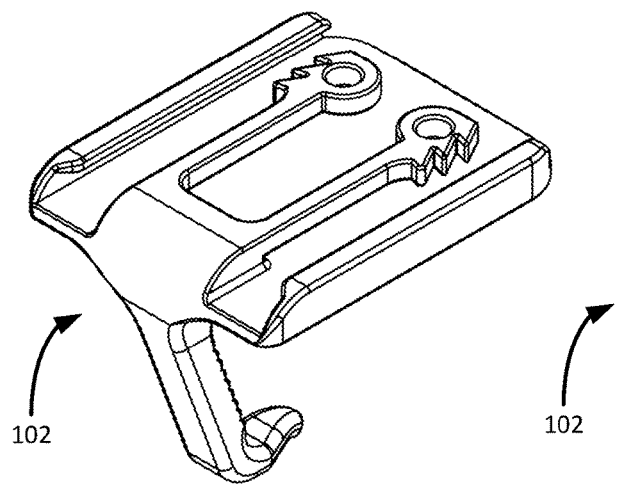
FIG. 16A and FIG. 16B are top perspective and top views, respectively, of the receiver member of the single leg embodiment of FIG. 14A.
Figure 16B:
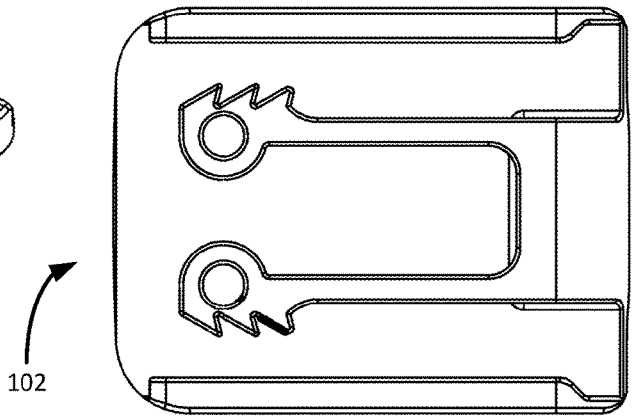

The dual ratchet assembly 134 includes a pair of ratchet arms 140 that extend forward from the insertion member base 130. Each of the ratchet arms 140 includes a linear rack consisting of a series of inward facing ratchet teeth 142 disposed on the interior side of each ratchet arm 140. FIG. 13A provides a close-up view of a first embodiment of the ratchet teeth 142. In this embodiment, the ratchet teeth 142 have an asymmetrical profile that permits advancement of the ratchet arms 140 in a forward direction, but resists retraction in a reverse direction. A relief 146 is located at the interior intersection between adjacent teeth 142. The relief 146 may facilitate the disengagement of the teeth 142 from the pawl teeth 124. The size, shape and number of ratchet teeth 142 may vary with application. Increasing the number of ratchet teeth 142 increases the number of positions in which the insertion member 104 can be secured within the receiver member 102. Increasing the depth of the ratchet teeth 142 increases the amount of deflection needed to release the pawl arms 120 from the ratchet arms 140. FIG. 13B presents a close-up view of a second embodiment of the ratchet teeth 142. In this embodiment, the ratchet teeth 142 do not include an interspersed relief 146 between each tooth 142. The embodiment depicted in FIG. 13B may be easier and more cost-effective to manufacture, while providing a full engagement with the corresponding pawl teeth 124.

Figure 2:
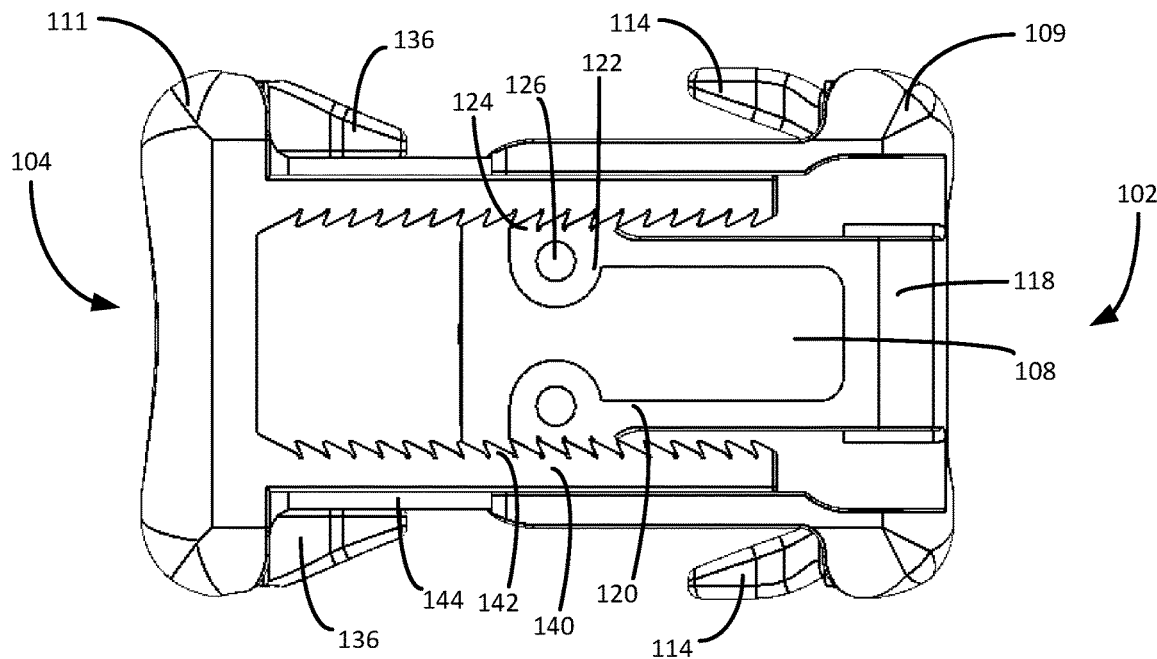
FIG. 2 is a top view of the sternal closure device of FIG. 1.

In exemplary embodiments, the geometry and configuration of the pawl teeth 124 is configured to match the geometry and configuration of the ratchet teeth 142. In both cases, each of the teeth 124, 142 is configured with sides that form acute angle. In some embodiments, the teeth 124, 142 each form a point with an angle less than 40°. In some embodiments, the sides of the teeth 124, 142 are positioned at about a 37° angle, with a slightly rounded tip (as best illustrated in FIGS. 13A and 13B). As illustrated in FIGS. 2 and 8, the heads 122 include a plurality of pawl teeth 124. In the embodiment depicted, each head 122 includes four pawl teeth 142. The use of multiple pawl teeth 142 increases the total contact area between the pawl teeth and the ratchet teeth 142 within the joint locking mechanism 106 to provide a stronger, more secure engagement between the receiver member 102 and the insertion member 104. The aggregate contact area is also increased as a result of the steep angle and length of each tooth within the pawl teeth 124 and ratchet teeth 142.

Each of the ratchet arms 140 includes an outward facing alignment tab 144 located on the exterior side of each ratchet arm 140. The alignment tabs 144 are sized and configured to fit closely within the channels 128 of the receiver member base 108. In exemplary embodiments, the extension of the alignment tabs 144 from the ratchet arms 140 contributes to each ratchet arm 140 having a substantially "L-shaped" cross section. The close fit between the alignment tabs 144 and the channels 128 prevents the insertion member 104 from rotating, tilting or lifting off the surface of the receiver member base 108. In this way, the channels 128, base 108 and alignment tabs 144 cooperatively restrict the relative movement between the insertion member 104 and receiver member 102 to a single linear longitudinal axis.

The joint locking mechanism 106 includes the combination of elements from the dual pawl assembly 112 and the dual ratchet assembly 134. Unlike prior art clamp-style sternal closure devices that employ rotating locks or spring-based ratchet systems, the joint locking mechanism 106 sternal closure device 100 includes a robust locking engagement between the dual pawl assembly 112 and dual ratchet assembly 134 that reduces the risk of unintentional separation or disengagement between the receiver member 102 and insertion member 104.

During use, the insertion member 104 and receiver member 102 contact opposing portions of the severed sternum. As the sternum is approximated, the insertion member 104 is introduced into the receiver member 102. The alignment tabs 144 of the ratchet arms 140 are captured within the channels 128 of the receiver member 102. As the insertion member 104 further advances into the receiver member 102, the dual ratchet assembly 134 engages the dual pawl assembly 112 to prevent the retraction of the insertion member 104 from the receiver member 102. As the insertion member 104 advances, the ratchet arms 140 force the pawl arms 120 to deflect inward against an opposing, outward-biased spring force produced by the pawl arms 120. Once the ratchet arms 140 are captured by the channels 128 and engaged with the heads 122 of the pawl arms 120, the pawl arms 120 apply the outward spring force against the ratchet arms 140. The pawl teeth 124 on the heads 122 of the pawl arms 120 are thus forced into an intermeshed connection with the ratchet teeth 142 on the ratchet arms 140. The orientation and configuration of the ratchet teeth 142 and pawl teeth 124 prevent the withdrawal of the insertion member 104 (as best illustrated in FIG. 2), and increase the closing strength and stability of the insertion member 104 while mated.

Importantly, the joint locking mechanism 106 increases the locked engagement of the dual pawl assembly 112 and the dual ratchet assembly 134 when the insertion member 104 and receiver member 102 are placed in tension. The orientation and configuration of the pawl teeth 124 and ratchet teeth 142 increase the outward lateral force applied by the pawl heads 122 against the ratchet arms 140, which is then transferred to, and opposed by, and the channels 128. In this way, an increasing tension force across the sternal closure device 100 caused by coughing or deep inhalation increases the engagement forces within the joint locking mechanism 106. The receiver member 102 and insertion member 104 are designed such that increased tensional forces are translated into increased lateral engagement forces through the joint locking mechanism 106 and captured within the channels 128 of the receiver member 102. This represents a significant improvement over prior art locking devices that rely on single-sided locking mechanisms or dual locking mechanisms that are not captured within a boxed receiver.

To release the insertion member 104, the dual pawl assembly 112 must be disengaged from the ratchet arms 140. The dual pawl assembly 112 can be selectively released by an operator by applying a compressive force to the heads 122 of the pawl arms 120 to cause the heads to deflect inward by a distance greater than the depth of the engagement between the ratchet teeth 142 and the pawl teeth 124. In exemplary embodiments, a release tool with a hinged plier mechanism is connected to the tool apertures 126 in the heads 122 so that leverage can be used to apply a compressive force sufficient to disengage the pawl teeth 124 on the heads 122 from the ratchet teeth 142 on the ratchet arms 140. Once the dual pawl assembly 112 has been released from the dual ratchet assembly 134, the insertion member 104 can be easily withdrawn from the receiver member 102.

It is clear that the present invention is well adapted to carry out its objectives and attain the ends and advantages mentioned above as well as those inherent therein. While embodiments of the invention have been described in varying detail for purposes of disclosure, it will be understood that numerous changes may be made which will readily suggest themselves to those skilled in the art and which are encompassed within the spirit of the invention disclosed herein and in the associated drawings and appended claims.

It is claimed:

1. A sternal closure device comprising:
   a receiver member, wherein the receiver member comprises:
     a receiver member base;
     channels extending along sides of the receiver member base, wherein each of the channels includes an upper overhang; and
     one or more receiver member legs extending from the receiver member base;
   a dual pawl assembly; and an insertion member, wherein the insertion member comprises:
an insertion member base;
one or more insertion member legs extending from the insertion member base; and
a dual ratchet assembly that is configured for capture within the receiver member, wherein the dual ratchet assembly further comprises a pair of ratchet arms that each have an L-shaped cross-section with an outward facing alignment tab that is configured to be captured tightly under the overhang of a corresponding one of the channels on the receiver member.

2. The sternal closure device of claim 1, wherein the receiver member comprises rounded shoulders above the one or more receiver member legs.

3. The sternal closure device of claim 1, wherein the dual pawl assembly comprises:
a pawl block; and
a pair of pawl arms extending from the pawl block.

4. The sternal closure device of claim 3, wherein the dual pawl assembly further comprises a pair of heads, wherein each of the pair of heads is located at a distal end of a corresponding one of the pair of pawl arms.

5. The sternal closure device of claim 4, wherein each of the heads comprises:
a plurality of outward facing pawl teeth; and
a tool aperture.

6. The sternal closure device of claim 5, wherein each of the pair of ratchet arms comprises:

a series of inward facing ratchet teeth, wherein the ratchet teeth are configured for an intermeshed engagement with the pawl teeth of a corresponding one of the pair of heads.

7. The sternal closure device of claim 1, wherein the insertion member comprises rounded shoulders above the one or more receiver member legs.

8. A sternal closure device comprising:
a receiver member that comprises channels with overhangs that form a boxed receiver;
an insertion member that comprises ratchet arms with alignment tabs that fit within the channels of the receiver member; and
means for releasably securing the insertion member within the receiver member.

9. The sternal closure device of claim 8, wherein the receiver member comprises:
a receiver member base; and
a pair of receiver member legs extending downward from the base and configured to engage a first side of a severed sternum.

10. The sternal closure device of claim 9, wherein the insertion member comprises:
an insertion member base; and
a pair of insertion member legs extending downward from the insertion member base and configured to engage a second side of a severed sternum.

* * * * *